US008025056B2

(12) United States Patent
Lewis

(10) Patent No.: US 8,025,056 B2
(45) Date of Patent: Sep. 27, 2011

(54) HYPERBARIC CHAMBER

(75) Inventor: Peter A. Lewis, Scotia, NY (US)

(73) Assignee: Hyperbaric Technologies, Inc., Amsterdam, NY (US)

( * ) Notice: Subject to any disclaimer, the term of this patent is extended or adjusted under 35 U.S.C. 154(b) by 663 days.

(21) Appl. No.: 12/029,822

(22) Filed: Feb. 12, 2008

(65) Prior Publication Data

US 2008/0210239 A1 Sep. 4, 2008

Related U.S. Application Data

(63) Continuation-in-part of application No. 11/481,899, filed on Jul. 7, 2006, now Pat. No. 7,634,999.

(51) Int. Cl.

| | |
|---|---|
| ***A61M 16/00*** | (2006.01) |
| ***A61G 10/00*** | (2006.01) |
| ***A61G 11/00*** | (2006.01) |
| ***A62B 18/02*** | (2006.01) |
| ***E04G 11/04*** | (2006.01) |

(52) U.S. Cl. ......... 128/205.26; 128/204.18; 128/202.12; 600/21; 600/22; 52/2.17

(58) Field of Classification Search ............. 128/204.18, 128/202.12, 205.26; 600/21, 22; 52/2.17
See application file for complete search history.

(56) References Cited

U.S. PATENT DOCUMENTS

| | | | |
|---|---|---|---|
| 1,294,188 | A | 2/1919 | Stelzner |
| 2,401,230 | A | 5/1946 | Colley |
| 2,731,055 | A | 1/1956 | Smith |
| 3,387,412 | A | 6/1968 | Kwake |
| 3,602,221 | A | 8/1971 | Bleicken |
| 3,729,022 | A | 4/1973 | Roach |
| 3,768,467 | A | 10/1973 | Jennings |
| 3,801,093 | A | 4/1974 | Jones |
| 4,103,369 | A | 8/1978 | Riordan |
| 4,106,504 | A | 8/1978 | York |
| 4,196,656 | A | 4/1980 | Wallace et al. |
| 4,294,242 | A | 10/1981 | Cowans |

(Continued)

FOREIGN PATENT DOCUMENTS

DE 3004156 A1 5/1980

(Continued)

OTHER PUBLICATIONS

International Search Report and Written Opinion of International Searching Authority for PCT/US08/85404 dated Feb. 4, 2009.

(Continued)

*Primary Examiner* — Patricia Bianco
*Assistant Examiner* — Nihir Patel
(74) *Attorney, Agent, or Firm* — Scott A. Felder; Wiley Rein LLP

(57) ABSTRACT

A portable hyperbaric chamber system includes a soft-sided, foldable hyperbaric chamber and a substantially rigid, removable, external support structure. The chamber generally includes a wall of a substantially non-breathable, soft-sided, and foldable material and an accessway sealable with a non-breathable closure so as to maintain a hyperbaric pressure within the chamber. The chamber also includes at least one fastener, such as a bolt or threaded stud, extending from the wall that permits the chamber to be removably attached to the support structure, thereby to maintain the chamber in an uncollapsed state when the chamber interior is not maintained at a hyperbaric pressure. The support structure includes structures complementary to the fasteners (e.g., apertures to pass bolts and locking knobs to secure bolts).

15 Claims, 7 Drawing Sheets

U.S. PATENT DOCUMENTS

| | | | | |
|---|---|---|---|---|
| 4,432,354 | A | 2/1984 | Lasley | |
| 4,509,513 | A | 4/1985 | Lasley | |
| 4,567,696 | A | 2/1986 | Malet | |
| 4,691,695 | A | 9/1987 | Birk et al. | |
| 4,736,762 | A | 4/1988 | Wayman | |
| 4,974,829 | A | 12/1990 | Gamow et al. | |
| 5,398,678 | A | 3/1995 | Gamow | |
| 5,402,775 | A | 4/1995 | Reneau | |
| 5,678,543 | A * | 10/1997 | Bower | 128/205.26 |
| 5,964,222 | A | 10/1999 | Kotliar | |
| 6,241,653 | B1 | 6/2001 | Gauger et al. | |
| 6,321,746 | B1 | 11/2001 | Schneider et al. | |
| 6,748,760 | B1 | 6/2004 | Cheng | |

FOREIGN PATENT DOCUMENTS

WO 2008010914 A2 1/2008

OTHER PUBLICATIONS

Operating and Reference Manual "Portable Mild Hyperbaric Chambers", Oxy Health Corporation, 2002.

International Search Report and Written Opinion of International Searching Authority in PCT/US07/15406 dated Jun. 4,2008.

* cited by examiner

HYPERBARIC CHAMBER

CROSS-REFERENCE TO RELATED APPLICATIONS

This application is a continuation-in-part of U.S. application Ser. No. 11/481,899, filed 7 Jul. 2006, now U.S. Pat. No. 7,634,999, which is hereby incorporated by reference as though fully set forth herein.

BACKGROUND OF THE INVENTION a. Field of the Invention

The instant invention relates generally to hyperbaric chambers. In particular, the instant invention relates to a portable hyperbaric chamber system including a removable external support structure.

b. Background Art

Certain activities, such as mountaineering and skiing, subject participants to reduced pressures. These reduced pressures can lead to what is commonly referred to as mountain sickness, with symptoms including nausea and headache. Other activities, such as diving and deep sea construction, subject participants to elevated pressures. If the participant returns to normal atmospheric pressures too rapidly, the participant may experience the detrimental health effects of decompression sickness.

To treat either mountain sickness or decompression sickness, it is known to place the patient in a high-pressure environment. Hyperbaric chambers are a convenient way to provide such a therapeutic environment. A hyperbaric chamber is a chamber in which a pressure greater than ambient, over and above the range of pressure variation encountered in the course of normal weather fluctuations, can be achieved. U.S. Pat. No. 4,974,829 to Gamow et al. ("Gamow") and U.S. Pat. No. 5,678,543 to Bower ("Bower"), the disclosures of which are hereby expressly incorporated by reference in their entireties, provide examples of such hyperbaric chambers.

Extant hyperbaric chambers, however, generally require a tradeoff between portability and capacity. That is, higher-pressure hyperbaric chambers tend to be more rigid and less portable, while portable chambers tend to be lower pressure. The hyperbaric chamber of Gamow, for example, is a portable chamber capable of achieving pressures up to about 10 psig, which are suitable for treating mild symptoms of pressure sickness. As one of skill in the art will recognize, higher pressure chambers are useful for treating more severe symptoms of decompression or mountain sickness, as well as for other conditions including carbon monoxide poisoning, wound healing, and burns.

Further, to the extent that a portable chamber is also collapsible, a rigid internal frame, generally made of metal, is often used to retain the uncompressed chamber in a substantially uncollapsed configuration. This aids in ingress to and egress from the chamber when it is in an unpressurized state (e.g., before or after treatment). Installation of this rigid frame into the interior of the chamber may be difficult and time consuming. In addition, an exposed metal frame within the chamber is not aesthetically pleasing and may also be physically uncomfortable for the chamber occupant.

BRIEF SUMMARY OF THE INVENTION

An object of the present invention is to provide a portable hyperbaric chamber system that retains an uncollapsed state when assembled, even though the chamber interior may not be pressurized, and without the use of a rigid internal frame.

In a first aspect, the present invention provides a hyperbaric chamber, including: a wall having an outer surface and an inner surface defining a chamber interior, the wall including a substantially non-breathable, soft-sided, and foldable material; an accessway into the chamber interior in the wall; a non-breathable closure configured to seal the accessway into the chamber interior such that a hyperbaric pressure may be maintained within the chamber interior; and at least one fastener, such as a bolt, threaded stud, or similar elongate fastener, extending from the outer surface of the wall and configured to be removably attached to a support structure to maintain the hyperbaric chamber in an uncollapsed state when the chamber interior is not maintained at a hyperbaric pressure.

In some embodiments, the at least one fastener passes entirely through the wall with a first end of the at least one fastener located within the chamber interior, and also including a seal adjacent an interface between the at least one fastener and the wall such that a hyperbaric pressure may be maintained within the chamber interior. For example, at least one non-breathable patch may cover the first end of the at least one fastener and be bonded to the interior surface of the wall. In other embodiments, the at least one fastener is attached to the outer surface of the wall.

Typically, the at least one fastener includes at least one fastener at a first end of the hyperbaric chamber and at least one fastener at a second end of the hyperbaric chamber. Preferably, the at least one fastener at the first end of the hyperbaric chamber includes a pair of fasteners at the first end of the hyperbaric chamber and the at least one fastener at the second end of the hyperbaric chamber includes a pair of fasteners at the second end of the hyperbaric chamber.

The invention also includes a support structure configured to maintain the hyperbaric chamber in an uncollapsed state when the chamber interior is not maintained at a hyperbaric pressure. The support structure generally includes at least one external rib to which the at least one fastener is configured to be removably attached, thereby pulling the wall of the hyperbaric chamber into the uncollapsed state. Preferably, the support structure includes a first external rib configured to wrap at least partially around the outer surface of the hyperbaric chamber proximate a first end thereof; and a second external rib configured to wrap at least partially around the outer surface of the hyperbaric chamber proximate a second end thereof, wherein each of the first rib and the second rib is configured to have at least one fastener of the hyperbaric chamber removably attached thereto, thereby pulling the wall of the hyperbaric chamber into the uncollapsed state. Optionally, the support structure further includes at least one cross-member connected to the first rib and the second rib, thereby maintaining a preset distance between the first rib and the second rib. It is desirable for the support structure (e.g., the at least one rib) to be substantially rigid (that is, only slightly elastically deformable, if elastically deformable if at all).

In another aspect, the invention provides a hyperbaric chamber system, generally including a soft-sided hyperbaric chamber and a support frame. The chamber generally includes: a wall having an outer surface and an inner surface that defines a chamber interior, the wall being of a substantially non-breathable, foldable material; a sealable accessway into the chamber interior in the wall; a closure configured to seal the accessway such that a hyperbaric pressure may be maintained within the chamber interior; a first elongate fastener extending from the outer surface of the wall proximate a first end of the chamber; and a second elongate fastener extending from the outer surface of the wall proximate a second end of the chamber.

The support frame generally includes: a first substantially rigid rib configured to wrap at least partially around the outer surface of the chamber proximate the first end thereof when removably attached to the first elongate fastener; and a second substantially rigid rib configured to wrap at least partially around the outer surface of the chamber proximate the second end thereof when removably attached to the second elongate fastener. The support frame optionally further includes at least one substantially rigid cross-member connected to the first substantially rigid rib and the second substantially rigid rib, thereby maintaining a preset distance therebetween.

An advantage of the present invention is that it provides an easily assembled portable hyperbaric chamber system.

Another advantage of the present invention is that it provides a hyperbaric chamber that retains an uncollapsed state even when the chamber is not pressurized, thereby aiding ingress to and egress from the chamber.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
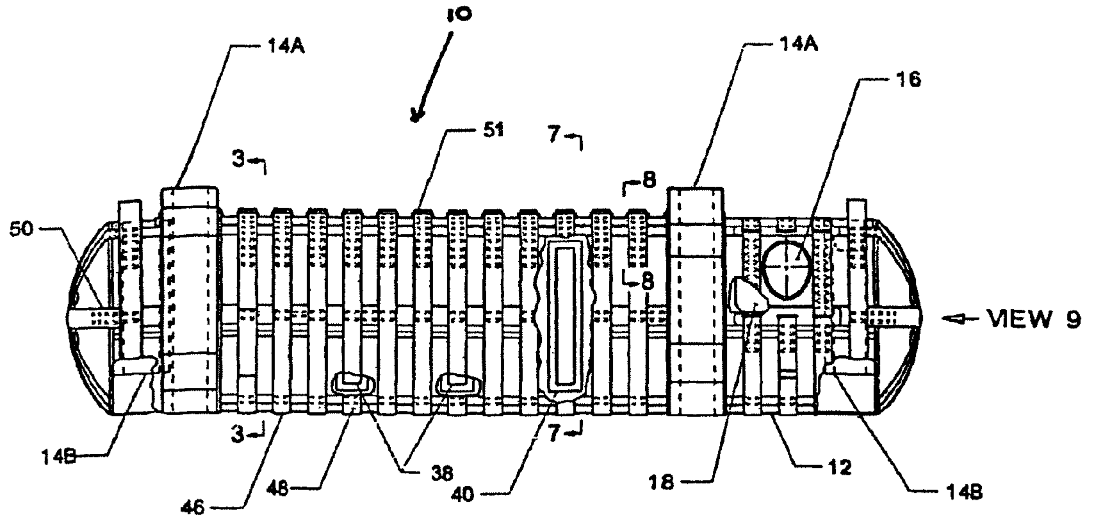
FIG. 1 is a partially broken away front view of a hyperbaric chamber according to an embodiment of the present invention.

The invention will now be described with reference to the drawing figures, in which like reference numerals refer to like parts throughout. An embodiment in accordance with the present invention provides a collapsible, pressurizable bladder and an inflatable support member supporting the bladder in a substantially uncollapsed configuration. The use of an inflatable support member facilitates rapid and simple installation of the support structure as compared to a rigid frame. Further, whereas a rigid frame is not aesthetically pleasing and is potentially physically uncomfortable, an inflatable support member is both attractive and more comfortable for the occupant of the chamber.

A system for treating symptoms of pressure sickness includes a collapsible chamber capable of sustaining hyperbaric pressures. A reinforcing harness is disposed on an outer surface of the chamber. The reinforcing harness permits the chamber to both operate at and sustain higher pressures than extant flexible, collapsible hyperbaric chambers. Thus, the instant invention can be used to create a therapeutic environment for treating both more severe pressure sickness symptoms and other undesirable conditions.

Figure 2:
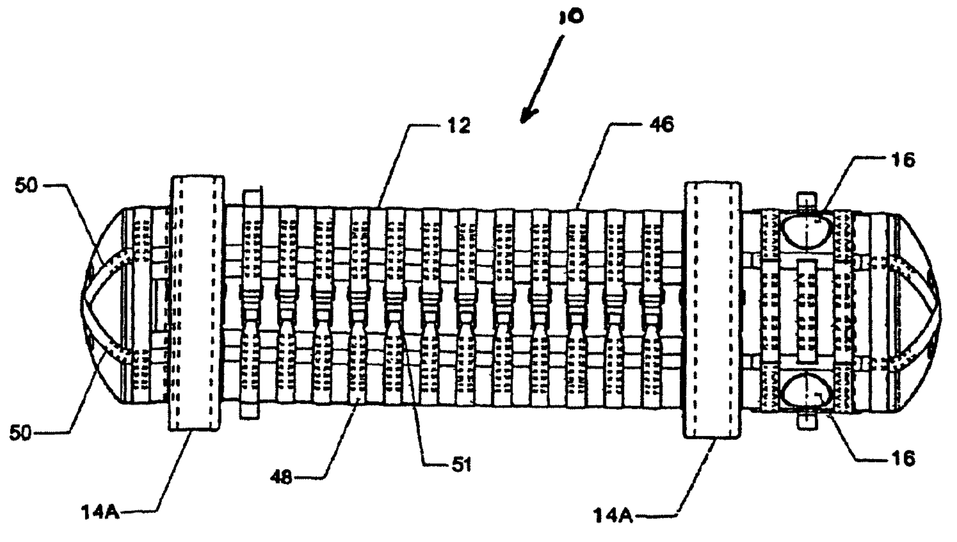
FIG. 2 is a top view of the hyperbaric chamber illustrated in FIG. 1.

An embodiment of the present invention is illustrated in FIGS. 1 and 2. A hyperbaric chamber 10 generally includes a collapsible, and therefore portable, pressurizable bladder 12 and an inflatable support member 14. Bladder 12 can be rendered pressurizable by forming it of an inherently substantially non-breathable material, such as a polyamide, nylon, or polyester. As used herein, the terms "non-breathable" and "air-impermeable" are largely synonymous, and refer to that which is substantially gas-impermeable, at least with respect to the major gaseous components of the atmosphere. Alternatively, bladder 12 may be made of a breathable material treated with a substantially non-breathable polymeric coating such as polyurethane or polyvinylchloride (PVC). Bladder 12 may also include one or more viewports 16, which may be of a flexible film type. In some embodiments of the invention, viewports 16 are polycarbonate-reinforced, for example with a LEXAN® shield 18. Shield 18 prevents deformation and potential failure of viewport 16 under pressure, and thereby facilitates increased pressures within bladder 12.

When pressurized, and thus uncollapsed, bladder 12 is substantially cylindrical in shape. Since bladder 12 is flexible and collapsible, however, it tends to collapse when unpressurized. A collapsed bladder 12 is difficult to enter or exit, and may cause discomfort for a patient occupying an unpressurized, and therefore substantially collapsed, bladder 12 during the initial and final moments of a treatment cycle. To address this, inflatable support member 14 supports bladder 12 in a substantially uncollapsed, substantially cylindrical configuration when depressurized, as shown in FIGS. 1 and 2.

In embodiments, hyperbaric chamber 10 includes multiple inflatable support members 14, for example two external inflatable support members **14*a* and two internal inflatable support members 14*b* located generally at opposing ends of bladder 12 and forming, in effect, a structural frame for bladder 12. It should be understood, however, that more or fewer inflatable support members 14 may be used without departing from the spirit or scope of the present invention. Inflatable support member 14 is, in some embodiments of the invention, an inflatable rib with curvature corresponding generally to the substantially cylindrical shape of the pressurized, uncollapsed bladder 12, though other configurations of inflatable support member 14**, such as longitudinal or radial support members, are also contemplated.

Figure 3:
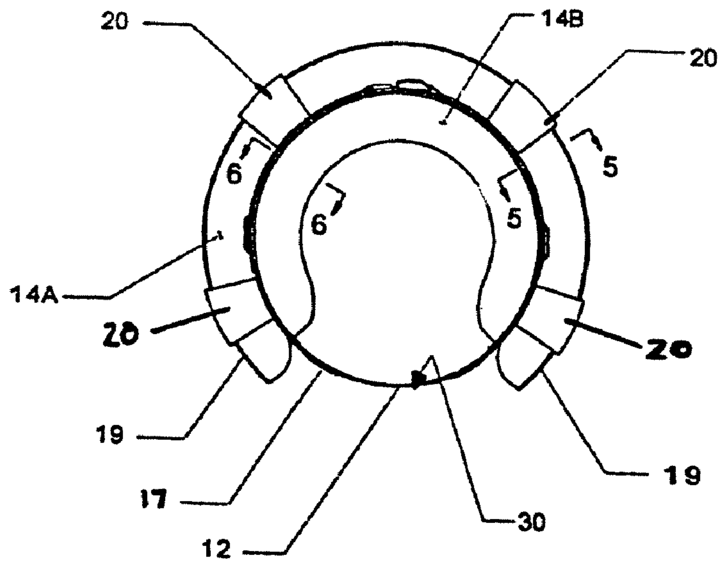
FIG. 3 is a cross-sectional view taken along line 3-3 in FIG. 1.

Referring now to FIG. 3, external inflatable support member **14*a* and internal inflatable support member 14*b* are shown supporting bladder 12 in a substantially uncollapsed, substantially cylindrical configuration. External support member 14*a* externally supports bladder 12 via an attachment to an exterior surface 17 of bladder 12. That is, external support member 14*a* pulls bladder 12 into a substantially uncollapsed configuration. External support member 14*a*, in particular flats 19 thereof, may also serve as a roll-prevention stand for bladder 12**.

Figure 4:
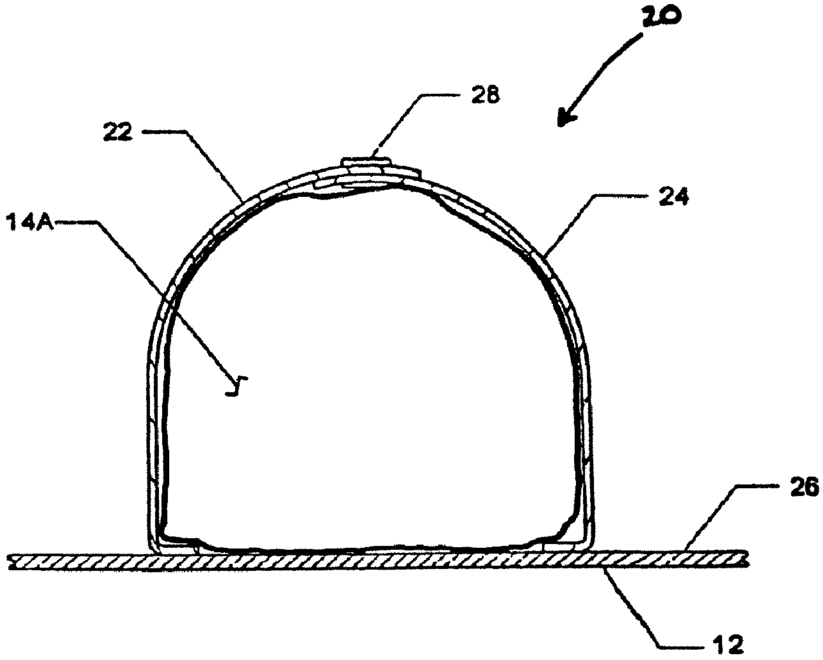
FIG. 4 illustrates a sleeve for attaching an inflatable support member to the bladder in a hyperbaric chamber according to the present invention.

FIG. 4 illustrates an attachment sleeve 20 for attaching external support member **14*a* to bladder 12. Multiple such attachment sleeves 20 may be used to secure external support member 14*a* to bladder 12. Attachment sleeve 20 includes first and second straps 22, 24, which are attached to bladder 12 via an attachment panel 26. First and second straps 22, 24 may alternatively be attached directly to exterior surface 17 of bladder 12. Straps 22, 24, attachment panel 26, and bladder 12 may be attached, for example, via sewing or heat seal. Straps 22, 24 are joined by a fastener 28, such as a snap, a button, a clasp, a toggle, laces, or a hook-and-loop fastener. In use, external support member 14***a* is placed between straps 22, 24 along exterior surface 17. Straps 22, 24 are then fastened about external support member 14*a*. It should be understood that this assembly may equally be accomplished with external support member 14*a* in an inflated, partially inflated, or completely deflated state. Other methods of attachment, including, but not limited to, permanently attaching external support member 14*a* to bladder 12, such as via sewing or heat seal, are also contemplated.

Returning now to FIG. 3, internal inflatable support member 14*b* supports bladder 12 in a substantially uncollapsed configuration via an abutment against an interior surface 30 of bladder 12. In embodiments, internal support member 14*b* is attached to interior surface 30, for example via a hook-and-loop fastener or a fastener similar to attachment sleeve 20. It should be understood from this disclosure and from practicing the invention, however, that, when inflated, internal support member 14*b* pushes bladder 12 into a substantially uncollapsed configuration regardless of any attachment between internal support member 14*b* and bladder 12. As with external support member 14*a*, the installation of internal support member 14*b* into bladder 12 may be accomplished with internal support member 14*b* in an inflated, partially inflated, or completely deflated state.

Figure 5:
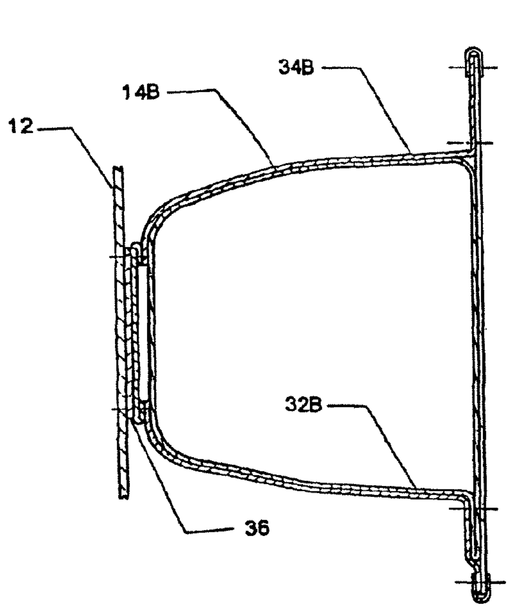
FIG. 5 is a cross-sectional view taken along line 5-5 in FIG. 3.
Figure 6:
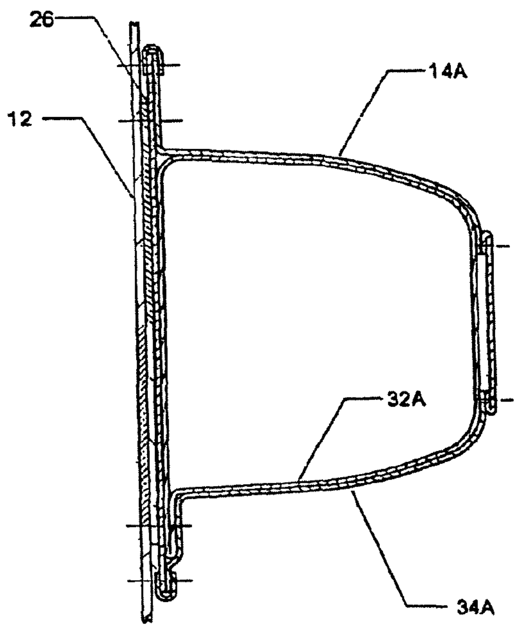
FIG. 6 is a cross-sectional view taken along line 6-6 in FIG. 3.

FIGS. 5 and 6, respectively, show the construction of external and internal support members 14*a*, 14*b*. External and internal support members 14*a*, 14*b* include air bladders 32*a*, 32*b* and jackets 34*a*, 34*b* substantially surrounding air bladders 32*a*, 32*b*. Like bladder 12, air bladders 32*a*, 32*b* may be formed of a substantially non-breathable material, or, alternatively, of a breathable material treated with a substantially non-breathable coating. Jackets 34*a*, 34*b* provide durability and reinforcement to support members 14*a*, 14*b*. Jackets 34*a*, 34*b* further provide a surface for attachment between support members 14*a*, 14*b* and attachment panel 26, in the case of external support member 14*a*, and hook-and-loop fastener 36, in the case of internal support member 14*b*. Jackets 34*a*, 34*b* may be made of polyester or nylon, though other materials are contemplated.

Figure 7:
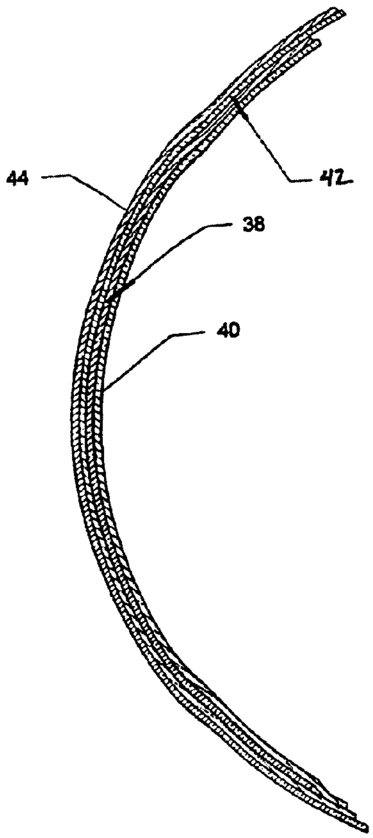
FIG. 7 is a cross-sectional view taken along line 7-7 in FIG. 1.

Returning now to FIG. 1, one or more stiffening staves 38, installed in corresponding stave sleeves 40, may also support bladder 12 in a substantially uncollapsed configuration. Stave 38 and sleeve 40 are also shown in FIG. 7, which further illustrates the construction of bladder 12. Bladder 12 includes a pressurizable internal shell 42 and an outer jacket 44 substantially surrounding shell 42. Internal shell 42 is substantially non-breathable. As with jackets 34 on inflatable support members 14, jacket 44 lends durability and reinforcement to pressurizable internal shell 42, and may be made of polyester or nylon, though other materials are contemplated.

As shown in FIGS. 1 and 2, hyperbaric chamber 10 further includes a reinforcing harness 46 substantially surrounding bladder 12 and disposed on exterior surface 17 thereof. Reinforcing harness 46 increases the pressure achievable within bladder 12. Reinforcing harness 46 may include both circumferential (or hoop) straps 48 and longitudinal straps 50 substantially surrounding bladder 12. Straps 48, 50 may be fastened by buckles 51. In some embodiments of the invention, reinforcing harness 46 includes a plurality of circumferential straps 48 interconnected by at least one longitudinal strap 50 to form a web-like reinforcing harness 46. It should be understood that more or fewer straps 48, 50 than shown may be utilized without departing from the spirit and scope of the present invention, and that the maximum pressure attainable within bladder 12 is related to the number and configuration of straps 48, 50 utilized.

Figure 8:
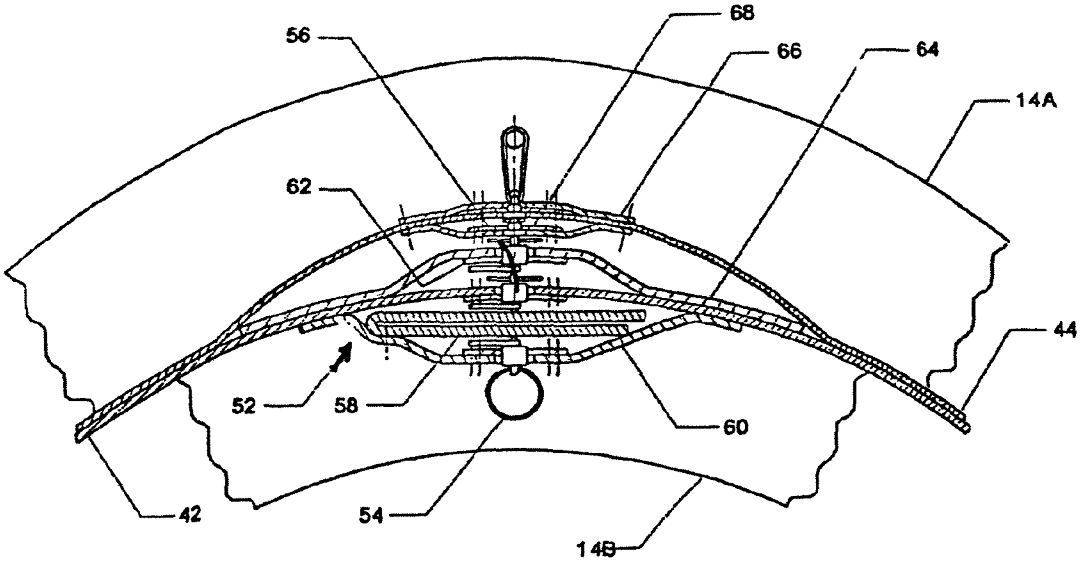
FIG. 8 is a cross-sectional view taken along line 8-8 in FIG. 1.

As shown in FIG. 8, bladder 12 incorporates an accessway to the interior thereof, including a substantially non-breathable closure 52. Non-breathable closure 52 is a multiple zipper closure including a first, inner zipper 54, a second, outer zipper 56, and a substantially air-impermeable gasket 58 disposed between first and second zippers 54, 56. In some embodiments of the invention, first and second zippers 54, 56 extend along substantially the entire length of bladder 12 to facilitate ingress and egress. Gasket 58 is, in some embodiments of the invention, a two-ply rubber flap. As illustrated, first zipper 54 is attached to a first zipper flap 60, while second zipper 56 is attached to internal shell 42. It should be understood, however, that other constructions and arrangements of first and second zippers 54, 56 are contemplated.

To close non-breathable closure 52 and pressurize bladder 12 from the outside of hyperbaric chamber 10, first zipper 54 is closed. Gasket 58 is then laid over first zipper 52, and second zipper 56 is closed. To close non-breathable closure 52 from the inside of hyperbaric chamber 10, the reverse process is followed. Non-breathable closure 52 will seal (that is, gasket 58 will be tightly sandwiched between first and second zippers 54, 56) when bladder 12 is pressurized.

To increase the pressure attainable within bladder 12, non-breathable closure 52 further includes a reinforcing zipper 62 installed in a reinforcing zipper flap 64. Reinforcing zipper 62 also reduces the likelihood of sudden decompression of bladder 12. As illustrated, reinforcing zipper 62 and reinforcing zipper flap 64 are installed outside of second zipper 56. It should be understood, however, that reinforcing zipper 62 and reinforcing zipper flap 64 could equally well be installed inside first zipper 54. Additional zippers 66, 68 may also be incorporated into jacket 44 or internal shell 42 to increase the strength of, and therefore the pressure attainable within, bladder 12.

Figure 9:
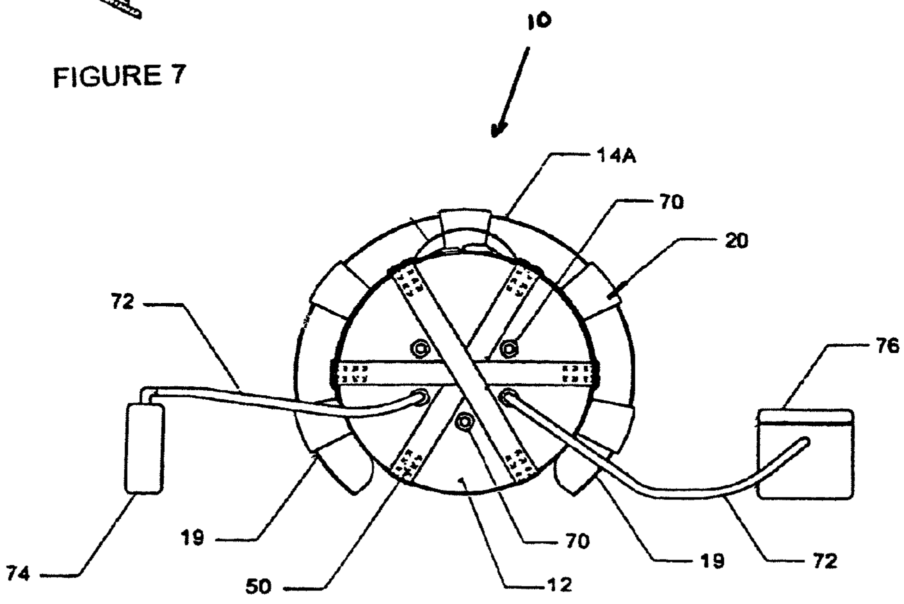
FIG. 9 is an end view of a hyperbaric chamber according to an embodiment of the present invention.

FIG. 9 is an end view of hyperbaric chamber 10. Visible are a number of pass-thrus 70 into the interior of bladder 12. Attached to at least one pass-thru 70 via a hose 72, and thus in fluid communication with the interior of bladder 12, is a source of pressurized air, such as compressed air tank 74. An appropriate valve may be provided adjacent one or both of compressed air tank 74 and pass-thru 70. Compressed air tank 74 may also be used to inflate support members 14.

Attached to a second pass-thru 70 via a second hose 72 is a cooling source 76. Cooling source 76, which, in some embodiments of the invention is a flexible bag filled with ice and water, conditions the air within bladder 12. Cooling source 76 may also be a rigid-walled container, and may further be insulated to preserve the cold contents thereof. Additional elements, for example air scrubbers, rebreathers, oxygen supplies, or chemical/biological decontamination filters, may also be placed in fluid communication with the interior of bladder 12 via additional pass-thrus 70.

Figure 10:
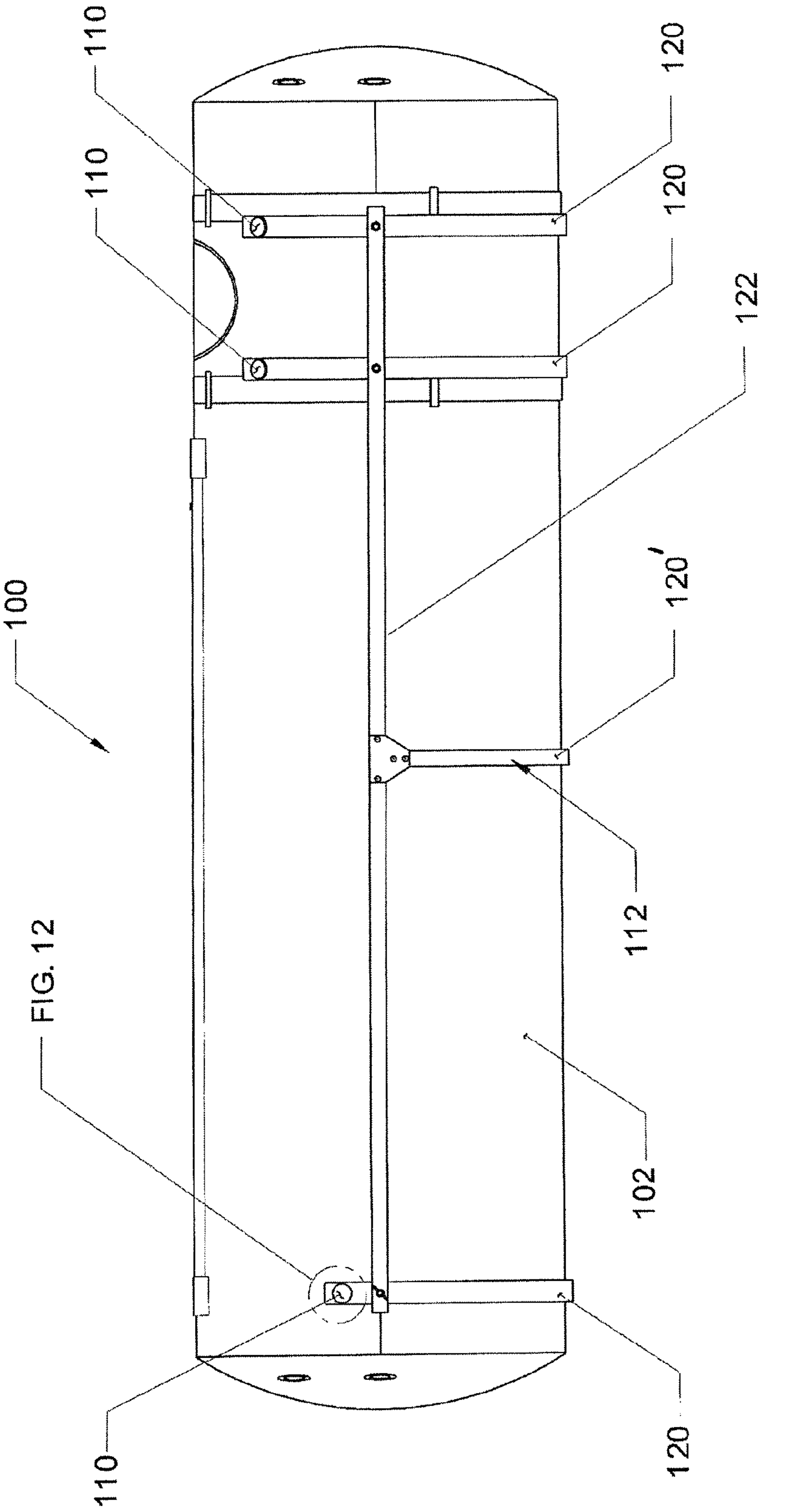
FIG. 10 is a side view of a hyperbaric chamber system including a substantially rigid external support frame according to an embodiment of the present invention.
Figure 11:
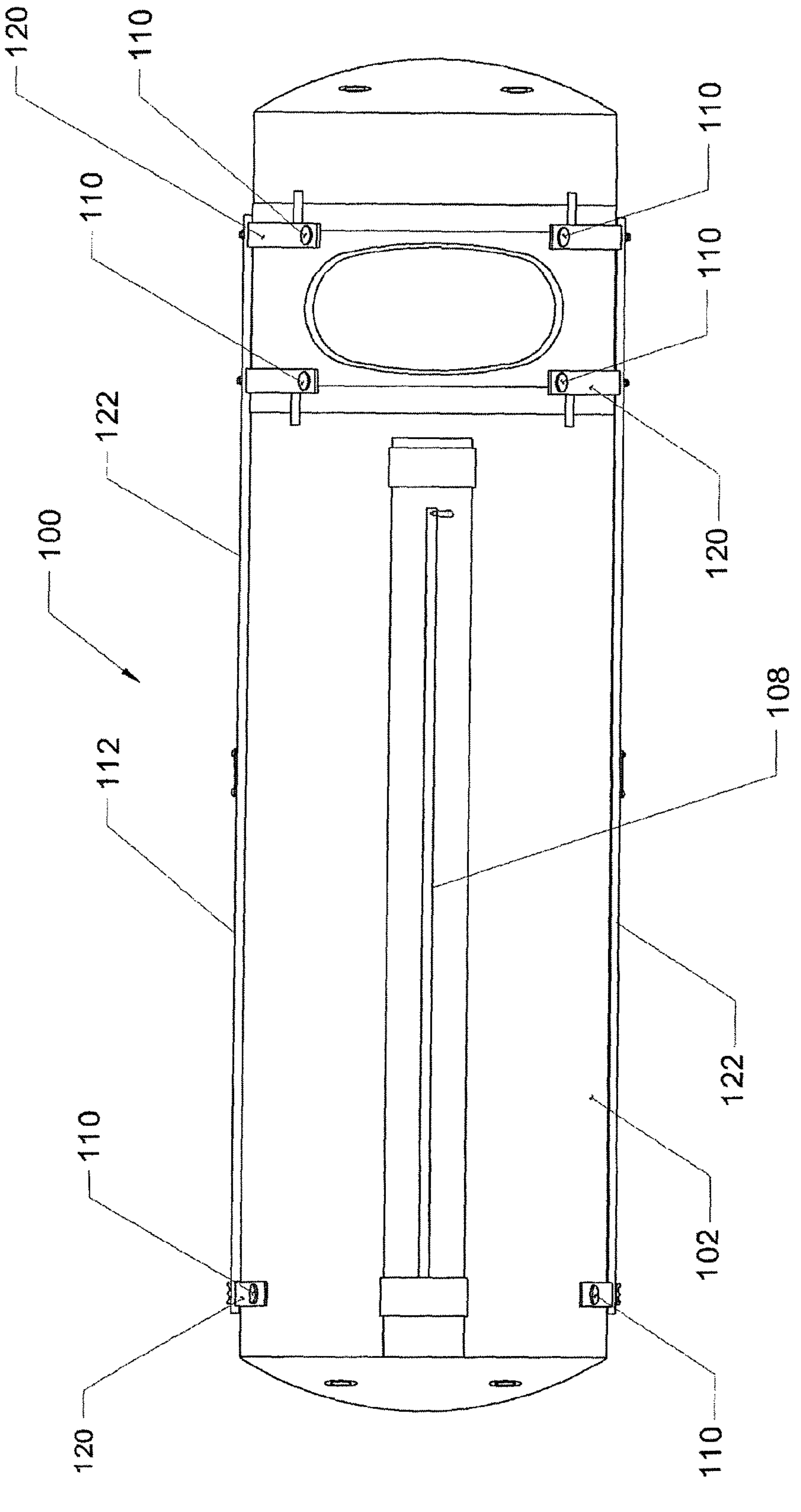
FIG. 11 is a top view of the hyperbaric chamber system illustrated in FIG. 10.
Figure 12:
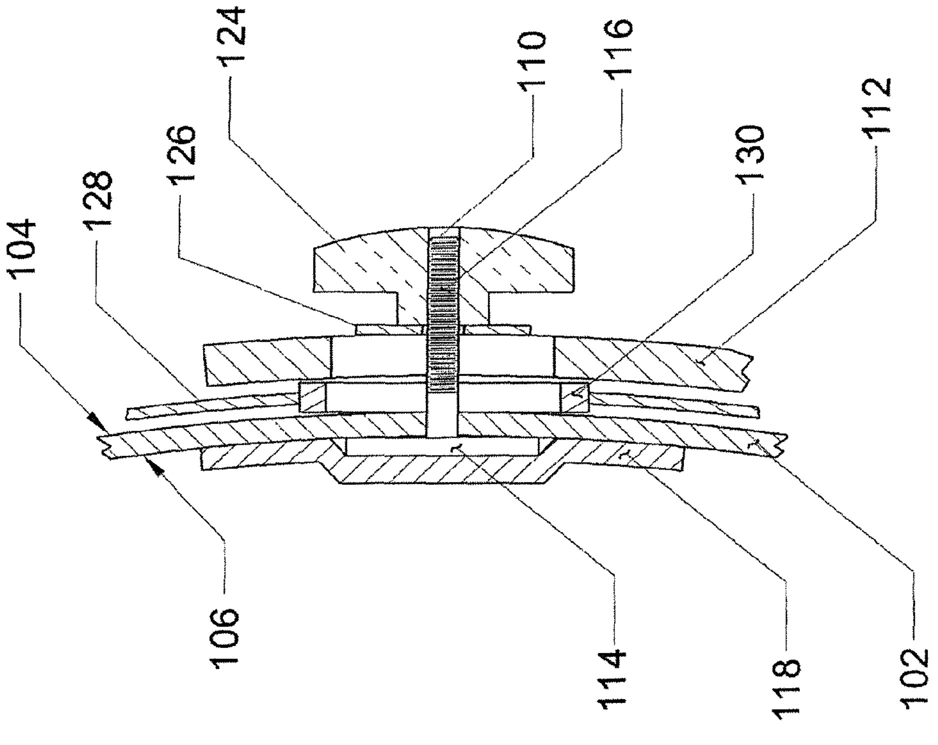
FIG. 12 is a cut-away view of the region detailed as FIG. 12 in FIG. 10.

Another aspect of the present invention is illustrated in FIGS. 10-12. FIGS. 10 and 11 illustrate a hyperbaric chamber 100 generally including a wall 102 of a substantially non-breathable, soft-sided, and foldable material. Wall 102 includes an outer surface 104 and an inner surface 106 (not shown in FIGS. 10 and 11, but illustrated in FIG. 12), with inner surface 106 defining the interior of hyperbaric chamber 100. An accessway into the interior of hyperbaric chamber 100 is also provided, as is a non-breathable closure 108 (for example, as described above) to seal the accessway such that a hyperbaric pressure may be maintained within the chamber interior. Of course, one of ordinary skill in the art will appreciate that there are many possible configurations of hyperbaric chamber 100 that are within the scope of the present teachings.

At least one fastener 110 (a total of six are shown in FIGS. 10 and 11, but more or fewer could be employed without departing from the scope of the present teachings) extends from outer surface 104 of wall 102 of hyperbaric chamber 100. Fasteners 110 are configured to be removably attached to a support structure 112, described in further detail below, so as to maintain hyperbaric chamber 100 in a substantially uncollapsed state when the chamber interior is not maintained at a hyperbaric pressure. Preferably, fasteners 110 are elongate fasteners such as bolts, threaded studs, or the like, configured for removable attachment to support structure 112. However, the use of other fasteners (e.g., hook-and-loop fasteners, snaps, etc.) is contemplated.

In some embodiments of the invention, for example as illustrated in FIG. 12, fasteners 112 pass entirely through wall 102 of hyperbaric chamber 100, such that a first end 114 (e.g., a head) of fastener 110 is located within the chamber interior and a second end 116 of fastener 110 is located outside hyperbaric chamber 110. A seal is provided adjacent the interface between fastener 110 and wall 102 such that a hyperbaric pressure may be maintained within the chamber interior without appreciable pressure leakage through the interface between fastener 110 and wall 102. For example, where the fastener is a bolt, an air-tight gasket may be provided between the head of the bolt and the inner surface of the wall. Alternatively, a non-breathable patch 118 may be bonded (e.g., sonically welded, laminated, chemically adhered, or the like) to inner surface 106 of wall 102 covering first end 114 of fastener 110 (as shown in FIG. 12).

In other embodiments of the invention, fasteners 110 are attached to outer surface 104 of wall 102. For example, fasteners 110 may be attached to outer surface 104 of wall 102 via a patch bonded (e.g., sonically welded, laminated, chemically adhered, or the like) to outer surface 104 of wall 102 and through which fasteners 110 pass, such that a portion of fastener 110 (e.g., the head of the bolt) is sandwiched between outer surface 104 of wall 102 and the patch.

There are many suitable arrangements for fasteners 110 on hyperbaric chamber 100. Preferably, there is at least one fastener 110 at a first end of the hyperbaric chamber (e.g., the head) and at least one fastener 110 at a second end of the hyperbaric chamber (e.g., the foot). More preferably, as illustrated in FIGS. 10 and 11, there is a pair of fasteners 110 at each end of the hyperbaric chamber, with the members of each pair being spaced apart from each other around the circumference of the chamber (shown to good advantage in FIG. 11). Of course, additional fasteners 110 may also be utilized without departing from the scope of the present invention. For example, as shown in FIGS. 10 and 11, a third pair of fasteners 110 may be provided proximate the head of the hyperbaric chamber.

Fasteners 110 are configured to be removably attached to external support structure or frame 112 such that wall 102 of hyperbaric chamber 100 is maintained in an uncollapsed state even though the chamber interior may not be pressurized. Support structure 112 generally includes at least one external rib 120, and preferably at least a pair of external ribs 120, configured to wrap at least partially around outer surface 104 of hyperbaric chamber 100 (e.g., a first rib configured to wrap at least partially around the head of the chamber and a second rib configured to wrap at least partially around the foot of the chamber). At least one cross-member 122 may also be connected to the ribs 120 in order to maintain a preset distance therebetween. Of course, additional members, such as intermediate rib 120', may also be provided if desired.

Preferably, support structure 112 is made of a substantially rigid material. The phrase "substantially rigid" refers to a material that may be capable of a small degree of elastic deformation, but which generally retains a preset shape, such as the curved shapes depicted in FIGS. 10 and 11. One suitable material for the support structure is aluminum, which is light weight and high strength, though one of ordinary skill in the art will recognize that other materials, including metals, metal alloys, and plastics, may also be employed consistent with the teachings herein.

The attachment of hyperbaric chamber 100 to support structure 112 via fasteners 110 will be described with reference to FIG. 12. (Hyperbaric chamber 100 and support structure 112 may be collectively referred to as a "hyperbaric chamber system.") As shown in FIG. 12, second end 116 of fastener 110 is inserted through an aperture in support structure 112. A knob 124 (and, optionally, one or more washers 126) may then be placed onto fastener 110. As knob 124 is tightened onto fastener 110, it will pull wall 102 of hyperbaric chamber 100 progressively against support structure 112 (note that FIG. 12 illustrates a jacket 128 with grommet 130 on the outside of wall 102). By repeating this process at each fastener 110, hyperbaric chamber 100 may be securely attached to support structure 112 in an uncollapsed state, even when the interior of hyperbaric chamber 100 is not under pressure, thereby aiding ingress to and egress from hyperbaric chamber 100. To disassemble the hyperbaric chamber system, the opposite process may be followed.

Although several embodiments of this invention have been described above with a certain degree of particularity, those skilled in the art could make numerous alterations to the disclosed embodiments without departing from the spirit or scope of this invention. For example, although an example of hyperbaric chamber 10 is shown using zippers 54, 56, 62, 66, and 68, it will be appreciated that other closures can be used. For example, one or more of zippers 54, 56, 62, 66, 68 may be replaced by a hook-and-loop fastener, a series of buttons, snaps, toggles, or clasps, or laces. As another example, fasteners 110 may be snaps configured to mate with complementary snaps on the interior of external ribs 120.

Further, though pressurized air source has been described and illustrated as a compressed air tank, other sources of compressed air, including, but not limited to, air compressors and pumps, are within the spirit and scope of the present invention.

Additionally, though hyperbaric chamber 10 has been described as useful for the treatment of mountain sickness or decompression sickness, it may also be used to isolate and treat an individual who has been exposed to a toxic hazard such as a chemical or biological weapon, and transferred safely under pressure and quarantine as a "hyperbaric stretcher."

One of ordinary skill in the art will also appreciate that the teachings herein may be practiced in various combinations without departing from the scope of the invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A hyperbaric chamber, comprising:

a wall having an outer surface and an inner surface defining a chamber interior, the wall comprising a substantially non-breathable, soft-sided, and foldable material;

an accessway into the chamber interior in the wall;

a non-breathable closure configured to seal the accessway into the chamber interior such that a hyperbaric pressure may be maintained within the chamber interior;

a first fastener extending outwardly from the outer surface of the wall at a first end of the hyperbaric chamber; and a second fastener extending outwardly from the outer surface of the wall at a second end of the hyperbaric chamber, wherein the first and second fasteners are configured to be removably attached to a support structure to maintain the hyperbaric chamber in an uncollapsed state when the chamber interior is not maintained at a hyperbaric pressure.

2. The hyperbaric chamber according to claim 1, wherein at least one fastener of the first and second fasteners passes entirely through the wall with a first end thereof located within the chamber interior.

3. The hyperbaric chamber according to claim 2, further comprising a seal adjacent an interface between the at least one fastener and the wall such that a hyperbaric pressure may be maintained within the chamber interior.

4. The hyperbaric chamber according to claim 3, wherein the seal comprises at least one non-breathable patch covering the first end of the at least one fastener and bonded to the interior surface of the wall.

5. The hyperbaric chamber according to claim 1, wherein at least one of the first and second fasteners is attached to the outer surface of the wall.

6. The hyperbaric chamber according to claim 1, wherein at least one fastener of the first and second fasteners comprises a threaded segment configured to be removably attached to a support structure.

7. The hyperbaric chamber according to claim 1, further comprising a third fastener at the first end of the hyperbaric chamber and a fourth fastener at the second end of the hyperbaric chamber.

8. The hyperbaric chamber according to claim 1, further comprising a support structure configured to maintain the hyperbaric chamber in an uncollapsed state when the chamber interior is not maintained at a hyperbaric pressure, the support structure comprising at least one external rib to which the first and second fasteners are configured to be removably attached, thereby pulling the wall of the hyperbaric chamber into the uncollapsed state.

9. The hyperbaric chamber according to claim 8, wherein the support structure comprises:

a first external rib configured to wrap at least partially around the outer surface of the hyperbaric chamber proximate a first end thereof; and a second external rib configured to wrap at least partially around the outer surface of the hyperbaric chamber proximate a second end thereof, wherein each of the first rib and the second rib is configured to have a respective one of the first and second fasteners of the hyperbaric chamber removably attached thereto, thereby pulling the wall of the hyperbaric chamber into the uncollapsed state.

10. The hyperbaric chamber according to claim 9, further comprising at least one cross-member connected to the first rib and the second rib, thereby maintaining a preset distance between the first rib and the second rib.

11. The hyperbaric chamber according to claim 8, wherein the at least one rib comprises at least one substantially rigid rib.

12. A hyperbaric chamber system, comprising:

a soft-sided hyperbaric chamber comprising:

a wall having an outer surface and an inner surface that defines a chamber interior, the wall comprising a substantially non-breathable, foldable material;

a sealable accessway into the chamber interior in the wall;

a closure configured to seal the accessway such that a hyperbaric pressure may be maintained within the chamber interior;

a first elongate fastener extend outwardly from the outer surface of the wall proximate a first end of the chamber; and a second elongate fastener extend outwardly from the outer surface of the wall proximate a second end of the chamber; and a support frame comprising:

a first substantially rigid rib configured to wrap at least partially around the outer surface of the chamber proximate the first end thereof when removably attached to the first elongate fastener; and a second substantially rigid rib configured to wrap at least partially around the outer surface of the chamber proximate the second end thereof when removably attached to the second elongate fastener.

13. The system according to claim 12, wherein the support frame further comprises at least one substantially rigid cross-member connected to the first substantially rigid rib and the second substantially rigid rib, thereby maintaining a preset distance therebetween.

14. The system according to claim 12, wherein each of the first elongate fastener and the second elongate fastener comprises a bolt having a first end attached to the outer surface of the wall.

15. The system according to claim 12, wherein each of the first elongate fastener and the second elongate fastener comprises a bolt passing through the wall, the bolt having a first end positioned within the chamber interior adjacent the inner surface of the wall.

* * * * *